United States Patent [19]
Barnett

[11] 4,199,525
[45] Apr. 22, 1980

[54] HYDROXYIMINO-SUBSTITUTED AMINOACETONITRILES

[75] Inventor: Charles J. Barnett, Indianapolis, Ind.

[73] Assignee: Eli Lilly and Company, Indianapolis, Ind.

[21] Appl. No.: 27,627

[22] Filed: Apr. 6, 1979

[51] Int. Cl.² ............................................ C07C 119/00
[52] U.S. Cl. ........................ 260/453 RW; 260/566 A
[58] Field of Search ................................ 260/453 RW

[56] References Cited
U.S. PATENT DOCUMENTS
3,144,485  8/1964  Benn et al. ................. 260/453 RW

*Primary Examiner*—Alan L. Rotman
*Assistant Examiner*—Robert C. Whittenbaugh
*Attorney, Agent, or Firm*—Dwight E. Morrison; Leroy Whitaker; Arthur R. Whale

[57] ABSTRACT

Hydroxyimino-substituted aminoacetonitriles, intermediates in the preparation of substituted 2-aminopyrazines, which latter compounds are intermediates in the preparation of insecticidal benzoylpyrazinylureas.

11 Claims, No Drawings

HYDROXYIMINO-SUBSTITUTED AMINOACETONITRILES

BACKGROUND OF THE INVENTION

1. Field of the Invention

This invention relates to novel hydroxy-imino-substituted aminoacetonitriles having utility as intermediates in the preparation of substituted 2-aminopyrazine compounds, which in turn are intermediates in the preparation of insecticidal benzoylpyrazinylureas disclosed and claimed in Belgian Pat. No. 833,288 (Mar. 11, 1976).

Description of the Prior Art

One of the main methods of synthesizing pyrazine compounds is that of building up the pyrazine ring system from aliphatic components to form the carbon-nitrogen bonds. Compounds useful in this method include α-aminonitriles, α-aminocarbonyl compounds, α, β-dicarbonyl compounds, and α-halogenoketones.

In the prior art, Sharp et al., *J. Chem. Soc.*, 932 (1951), describe the condensation of α-aminonitriles with oximinomethyl ketones to yield 3,5-disubstituted 2-aminopyrazine-1-oxides, which are then heated with sodium hydrosulphite to reduce the oxides to yield 3,5-disubstituted 2-aminopyrazines. This reference teaches that the efficiency of the general reaction is decreased by the replacement of alkyl with aryl groups.

In another reference, Taylor et al., *J. Am. Chem. Soc.* 95, 6407–6412 (1973), describe the condensation of α-aminocyanoacetamide with an oximinoketone, for example, oximinoacetophenone or oximinoacetone, in glacial acetic acid solution, to yield 2-amino-3-carbamoyl-5-substituted-pyrazine-1-oxides. The products are used in pteridine syntheses.

Taylor et al., *J. Am. Chem. Soc.* 90, 2424 (1968), describe the condensation of ethyl α-aminocyanoacetate with isonitrosoacetone (oximinoacetone) in glacial acetic acid, to yield 2-amino-3-carbethoxy-5-methyl-pyrazine-1-oxide. This product is also useful in the syntheses of pteridines.

Also in the prior art is Masaki et al., *Bull, Chem. Soc. Japan*, 36, 922 (1963), which discloses the reaction of α-halo oximes with amines. The product thereby obtained is reductively cyclized using Raney nickel catalyst to yield a piperazinone.

Also included in the prior art are Masaki et al., *J. Org. Chem.*, 29, 3165 (1964), and Masaki et al., *J. Org. Chem.* 31, 4143 (1966), both of which references disclose the reaction of protected α-aminohydroxamic acid with an α-chloro oxime, followed by removal of the oxime and O-benzyl groups, and treatment with ammonia to yield aspergillic acid-type compounds.

SUMMARY OF THE INVENTION

This invention relates to novel hydroxy-imino-substituted aminoacetonitriles, intermediates in the preparation of substituted 2-aminopyrazines, which latter compounds are intermediates useful in the preparation of insecticidal benzoylpyrazinylureas.

DESCRIPTION OF THE PREFERRED EMBODIMENT

This invention relates to novel hydroxy-imino-substituted aminoacetonitrilesof the following formula (I)

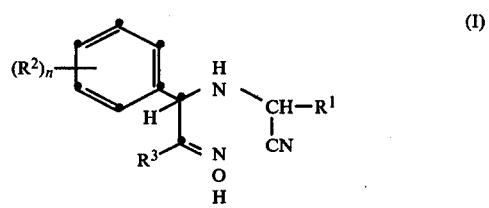

wherein
$R^1$ is hydrogen or $C_1$–$C_4$ alkyl;
$R^2$ is hydrogen, halo, $C_1$–$C_3$ alkyl, or trifluoromethyl;
n is 0, 1 or 2, with the proviso that when n=2, only one ortho position may be substituted; and
$R^3$ is $C_1$–$C_4$ alkyl.

These compounds of formula (I) are useful as the intermediates which are cyclized to yield the substituted 2-aminopyrazines of the following formula

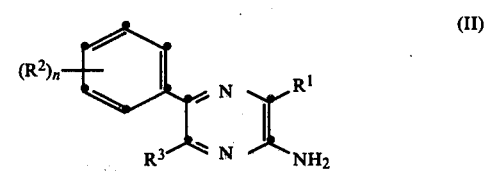

wherein $R^1$, $R^2$, $R^3$, and n have the same values as hereinbefore. Thus, a hydroxyimino-substituted aminoacetonitrile of Formula (I) is mixed with an acid selected from the group consisting of polyphosphoric acid, 85% phosphoric acid, and a mixture of phosphoric acid with phosphorus pentoxide, and then the mixture is heated at a temperature of from about 50° to about 140° C., for from about ½ to about 4 hours, to obtain a 2-aminopyrazine of Formula (II) above. These 2-aminopyrazine compounds are then used in the preparation of insecticidal benzoylpyrazinylureas disclosed and claimed in Belgian Pat. No. 833,288 (Mar. 11, 1976). This method of preparation of the compounds of Formula (II) is disclosed and claimed in U.S. application Ser. No. 27,630, filed of even date with the present application.

In the above formulae, $C_1$–$C_3$ alkyl represents methyl, ethyl, n-propyl, or isopropyl.

Also in the above formulae, $C_1$–$C_4$ alkyl represents methyl, ethyl, n-propyl, isopropyl, n-butyl, sec.-butyl, t-butyl, or isobutyl.

Halo represents bromo, chloro, fluoro, or iodo.

The novel hydroxyimino-substituted aminoacetonitriles of formula (I), supra, are prepared by allowing an aminoacetonitrile (III) to react with an α-chloro or α-bromo oxime (IV), according to the following reaction sequence:

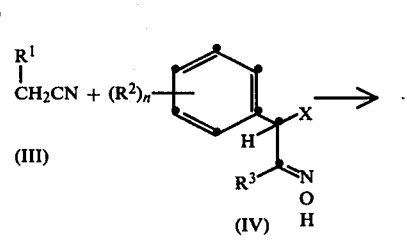

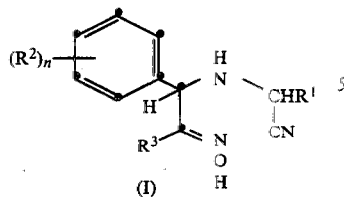

wherein $R^1$, $R^2$, $R^3$, and n have the same assigned values as set forth hereinbelow, and X is chloro or bromo.

In carrying out the reaction sequence set forth hereinbefore, an aminoacetonitrile of formula (III) is allowed to react with an α-chloro or α-bromo oxime of formula IV in a suitable solvent in the presence of an acid uptake agent, which agent neutralizes the hydrogen halide formed during the reaction. The α-chloro oxime compounds are preferred for use in this reaction because of the ready availability of nitrosyl chloride for use in their preparation. Only the α-chloro oximes will therefore be used to illustrate the teachings set forth in this specification. However, the α-bromo oximes would be expected to react in the same manner as the α-chloro oximes do in the preparation of the novel hydroxyimino-substituted amionoacetonitrile compounds. Suitable solvents include chloroform, methylene chloride, tetrahydrofuran, benzene and chlorobenzene, with the solvent of choice being selected from the group consisting of chloroform, and methylene chloride. Suitable acid uptake agents include the aminoacetonitrile itself, as well as those non-nucleophilic bases which are more basic that aminoacetonitrile, and include tertiary amine bases such as triethylamine, trimethylamine, tributylamine, and N-methylmorpholine, with triethylamine being the agent of choice.

Thus, the aminoaceotonitrile, either as the free base, or as an acid addition salt, e.g., the hydrochloric acid addition salt, or a like acid addition salt, is suspended in a solvent. When the aminoacetonitrile is used in the form of its acid addition salt, two moles of an acid uptake agent are added to the suspension. One mole serves to prepare the aminoacetonitrile as the free base, and the second mole serves to provide for neutralizing the hydrogen chloride formed during the reaction of the aminoacetonitrile and the α-chloro oxime. To the mixture of aminoacetonitrile free base, solvent, and acid uptake agent, cooled to a temperature between about −5° to about 25° C., there is added, with stirring, a solution of the α-chloro oxime, for example 1-chloro-1-phenyl-2-propanone oxime, in the same solvent, at such a rate as to make possible the ready maintenance of the temperature of the mixture in the range of from about −5° to about 25° C. At the completion of the addition, the reaction mixture is allowed to warm to room temperature with continued stirring over a period of about 1 hour.

The reaction mixture is washed successively with portions of water, and saturated aqueous sodium chloride, and the organic layer separated and dried, either over a suitable drying agent, or by filtering through a filterpad of the drying agent.

The dried solution of the crude hydroxy-imino-substituted aminoacetonitrile is reduced to about one-half its volume by evaporating the solvent. There is added to the reduced volume of solution an amount of a hydrocarbon solvent selected from the group consisting of hexane, pentane, heptane, and cyclohexane, sufficient to restore the original volume. The mixture is stirred at about room temperature, during which operation the product crystallizes. The product isolated by this procedure in the instant illustration is [[2-(hydroxyimino)-1-(phenyl)propyl]-amino]acetonitrile, having a melting point of about 96°–97.5° C.

It should be noted that if the phenyl group of the α-chloro oxime is substituted in the ortho position ($R^2$=halo or $C_1$–$C_3$ alkyl), the yield of the subsequent hydroxyimino-substituted aminoacetonitrile of Formula (I), supra, can be appreciably lower due to steric factors.

It is also possible to start with the appropriately substituted sytrene and to proceed to the hydroxyimino-substituted aminoacetonitrile without isolation of or crystallization of the intermediate α-chloro oxime. Thus, the preparation of the α-chloro oxime is carried out as previously described, using as the solvent the solvent to be used in the preparation of the hydroxyimino-substituted aminoacetonitrile. At the completion of the reaction between the substituted styrene and the nitrosyl chloride to yield the α-chloro oxime, the solution containing the crude α-chloro oxime is washed with water and the organic layer containing the crude α-chloro oxime is added directly to the mixture of aminoacetonitrile (either as the free base or as an acid addition salt, e.g., the hydrochloride salt), acid uptake agent, and solvent, the solvent being the same one employed in the preparation of the α-chloro oxime. The reaction is allowed to proceed for the requisite period of time to bring about substantially complete formation of the hydroxyimino-substituted aminoacetonitrile. The product is isolated in the same manner as previously described.

The preparation of the α-chloro oximes used in synthesizing the novel hydroxyimino-substituted aminoacetonitriles is known in the art, and can be described as follows. A styrene derivative, for example β-methylstyrene, is dissolved in an inert solvent such as methylene chloride or chloroform, the solution cooled to a temperature of about 0° to −5° C., and the solution saturated with anhydrous hydrogen chloride. The flow of anhydrous hydrogen chloride is then continued while nitrosyl chloride is added to the solution. Stirring and introduction of anhydrous hydrogen chloride are both continued while the reaction mixture is allowed to warm to room temperature over a period of about ½ hour. The reaction mixture is then purged with nitrogen for about ½ hour to remove the excess hydrogen chloride. The reaction mixture is washed successively with water and aqueous sodium chloride solution, and dried over a suitable drying agent, for example, anhydrous sodium sulfate. The drying agent is filtered off and the filtrate concentrated in vacuo to yield an oil, which is the crude α-chloro oxime. Since α-chloro oximes are thermally unstable, excessive heating is to be avoided during the work-up. The oil is taken up in hexane, and the crystalline product which forms is filtered off. In the instant illustration, the product is identified as 1-chloro-1-phenyl-2-propanone oxime, having a melting point of about 90°–92° C. The other α-chloro oximes used herein are prepared by the same general procedure.

While the above description utilizes nitrosyl chloride and hydrogen chloride in preparing the α-chloro oxime, it is to be expected that the same general procedure can be used to prepare α-bromo oximes, utilizing nitrosyl bromide and hydrogen bromide to react with an appropriately substituted sytrene.

With the exception of three compounds, the styrene compounds disclosed herein to be utilized for preparing the α-chloro oximes ae known and their preparations are published in the prior art. The compounds not previously prepared are synthesized following well-known published procedures. Thus, 2-bromobenzaldehyde is allowed to react with a Grignard reagent, ethyl magnesium bromide in anhydrous ether, to yield 1(2-bromophenyl)propanol. This propanol derivative is then dehydrated by refluxing it in toluene in the presence of a catalytic quantity of p-toluenesulfonic acid to yield the desired 1-bromo-2-(1-propenyl)benzene. Another previously unknown substituted styrene, namely, 1,2-dichloro-4-(1-propenyl) benzene is prepared by the same general procedure from 3,4-dichlorobenzaldehyde and ethyl magnesium bromide, followed by dehydration of the intermediate substituted propanol.

The third styrene compound not previously known is 1-ethyl-4-(1-propenyl) benzene, and it too is prepared by procedures apprearing in the literature. Thus, the condensation of ethylbenzene with propionyl chloride in the presence of aluminum chloride in a Friedal-Crafts reaction yields the known 4-ethylpropiophenone. This ketone is readily reduced using sodium borohydride to yield 1-(4-ethylphenyl)propanol, which is dehydrated by heating with potassium bisulfate, to yield the desired 1-ethyl-4-(1-propenyl)- benzene.

The following are descriptions of the preparation of the three new substituted styrenes, together with descriptions of the syntheses of several intermediate α-chloro oximes useful to prepare the novel hydroxyimino-substituted aminoacetonitriles of this invention.

PREPARATION 1

1-Bromo-2-(1-propenyl) benzene

This compound was prepared stepwise.
Step 1.

A solution of 34.46 g. (0.186 moles) of 2-bromobenzaldehyde in 93 ml. of anhydrous ethyl ether was added over a period of 15 minutes to a mixture of 75.6 ml. of a 2.71 M solution of ethyl magnesium bromide in 186 ml. of anhydrous ether held at a temperature of about 15° C. The reaction mixture was allowed to stand overnight at room temperature, after which it was cooled while 32 ml. of an aqueous 25% ammonium chloride solution was added. The ether was decanted from the solid residue, which residue was washed with ether and the washings added to the original ether layer. The combined ether layers were dried over anhydrous magnesium sulfate. The drying agent was filtered off and the ether solution concentrated to yield a light yellow oil weighing 32.21 g.

The oil was identified by NMR spectrum as 1-(2-bromophenyl) propanol.
Step 2.

A mixture of 25 g. (0.116 moles) of 1-(2- bromophenyl)propanol (prepared in Step 1), 80 ml. of toluene, and 1.0 g. of p-toluenesulfonic acid was refluxed under a Dean-Stark water separator for about 4 hours. The reaction mixture was then cooled, stirred for about 15 minutes with 20 ml. of 5 N aqueous sodium hydroxide solution, and the aqueous layer separated and discarded. The organic layer was washed with 3 portions of water and dried over anhydrous sodium sulfate. The drying agent was filtered off and the filtrate concentrated to yield crude product weighing 20.65 g. A portion weighing 19.5 g. was distilled to yield product having a boiling point of about 82°-85° C./3-4 mm., and identified by NMR spectrum as 1-bromo-2-(1-propenyl) benzene.

Following the same general procedures, and using appropriate starting materials, the following compound was prepared and identified.

PREPARATION 2

1,2-Dichloro-4-(1-propenyl)benzene

Step 1.

1-(3,4-Dichlorophenyl)propanol, as a dark yellow liquid, weighing 40.02 g., from 36.0 g. (0.20 mole) of 3,4-dichlorobenzaldehyde and 77.6 ml. of a 2.71 M solution of ethyl magnesium bromide.

Step 2.

1,2-Dichloro-4-(1-propenyl) benzene, as a dark amber liquid, weighing 29.61 g., from 40.02 g. (0.195 moles) of 1-(3,4-dichlorophenyl)propanol, 100 ml. of toluene, and 1.0 g. p-toluenesulfonic acid. Identified by NMR spectrum.

PREPARATION 3

1-Ethyl-4-(1-propenyl)benzene

This compound was prepared stepwise.
Step 1.

To a solution of 19 g. (0.117 moles) of 4-ethylpropriophenone in 30 ml. of ethanol, there was added dropwise a solution of 1.76 g. of sodium hydroxide, 1.4 g. of sodium borohydride, and 17.6 ml. of water. As addition proceeded, an exothermic reaction occurred and the temperature rose to about 35° C., and then as addition continued, to about 75° C., after which the reaction temperature dropped to about room temperature. The reaction mixture was stirred at room temperature for about 1 hour. It then was stirred and heated at about 70°-75° C. for about two hours, after which the heating and stirring was continued overnight at this temperature. The reaction mixture was allowed to cool. There was then added a solution of 0.6 g. of sodium hydroxide and 0.47 g. of sodium borohydride in 6 ml. of water, and the reaction mixture again heated and stirred at about 70°-75° C. overnight.

The reaction mixture was cooled, diluted with water, and the organic layer separated. The aqueous layer was extracted with three portions of ether, and the aqueous layer discarded. The ether extracts were combined with the original organic layer, and the combination washed successively with water, aqueous sodium bicarbonate solution, and saturated aqueous sodium chloride solution, and then dried over anhydrous magnesium sulfate.

The drying agent was filtered off, the solvent evaporated in vacuo and the residual oil distilled to yield product having a boiling point of about 173°-176° C./100 mm. The product was identified by NMR spectrum as 1-(4-ethylphenyl)propanol.

Step 2.

In a 50 ml. 3-neck round bottom flask equipped with a non-pressure-equalizing addition funnel, a jacketed, variable take-off distillation head, and a magnetic stirring bar, was placed 15 g. (0.11 moles) of crystalline potassium bisulfate. The pressure in the flask was reduced to about 90 mm. and, while the potassium bisulfate was magnetically stirred, the flask and contents were heated in an oil bath to a temperature of about 220°-230° C., and there was added dropwise 60 g. (0.365 moles) of 1-(4-ethylphenyl)propanol to the potassium bisulfate in the flask. During the addition, some material having a boiling point of about 125°–135° C./90 mm. distilled out of the reaction mixture. After the addition was complete, the distillation was continued at the reduced pressure of 90 mm. until distillation ceased. The pressure was then reduced to 50 mm., and distillation continued at that pressure until distillation again ceased. Ether was added to the distillate, the aqueous layer was separated and discarded, and the ether layer dried over anhydrous magnesium sulfate. The drying agent was filtered off and the ether removed in vacuo to leave 48.3 g. of a clear oil. The oil was identified by NMR spectrum as 1-ethyl-4-(1-propenyl)benzene.

PREPARATION 4

1-Chloro-1-phenyl-2-propanone oxime

A solution of 34.65 g. (0.294 moles) of β-methylstyrene in 300 ml. of chloroform was stirred and cooled to a temperature of about 0° to −3+ C., and while this temperature was maintained, the solution was saturated with anhydrous hydrogen chloride. To the solution there was added 20.2 g. (0.307 moles) of nitrosyl chloride, with a simultaneous flow of anhydrous hydrogen chloride sufficient to give an acid test at the vent from the reaction flask. The addition of the nitrosyl chloride took about 50 minutes. The reaction mixture was allowed to stir and warm to room temperature over a period of about 30 minutes, with a continued flow of anhydrous hydrogen chloride at about 60 ml. per minute. At the end of that time, the excess gases were purged from the system using dry nitrogen, the purge being carried out for about 30 minutes. The reaction mixture was washed twice with 150 ml. portions of water, followed by a wash with an aqueous solution of sodium chloride. The organic layer was dried over anhydrous sodium sulfate for about 10 minutes and the drying agent was filtered off. The filtrate was concentrated at reduced pressure to yield an oil which was stirred while 50 ml. of hexane was added. Crystals quickly formed while the mixture was stirred at room temperature for about 30 minutes. After cooling in the refrigerator over the weekend, the cold mixture was again stirred for about 15 minutes, filtered, and the solid on the filter washed with 50 ml. of cold hexane. There was obtained 38.12 g. (70.7% yield) of a product having a melting point of about 90°–92 C., and identified as 1-chloro-1-phenyl-2-propanone oxime.

| Analyses calculated for $C_9H_{10}ClNO$: | | |
|---|---|---|
| | Theoretical | Found |
| C | 58.87 | 59.03 |
| H | 5.49 | 5.20 |
| N | 7.63 | 7.69 |
| Cl | 19.31 | 19.30 |

Following the general procedure of Preparation 4, additional α-chloro oximes were prepared and identified.

PREPARATION 5

1-(2-Bromophenyl)-1-chloro-2-propanone oxime, as an oil, weighing 8.97 g., from 8.2 g. (0.042 moles) of 1-bromo-2-(1-propenyl)benzene and 3.0 g. (0.046 moles) of nitrosyl chloride. An analytical sample recrystallized from benzenehexane had a melting point of about 121°–122.5° C.

| Analyses calculated for $C_9H_9BrClNO$: | | |
|---|---|---|
| | Theoretical | Found |
| C | 41.18 | 40.97 |
| H | 3.46 | 3.23 |
| Br | 30.44 | 30.63 |
| Cl | 13.50 | 13.26 |
| N | 5.34 | 5.37 |

PREPARATION 6

1-(3-Bromophenyl)-1-chloro-2-propanone oxime, as an oil, weighing 16.47 g., from 12.5 g. (0.063 moles) of 1-bromo-3-(1-propenyl)benzene and 4.36 g. (0.066 moles) of nitrosyl chloride. The product was identified by its NMR spectrum.

PREPARATION 7

1-(4-Bromophenyl)-1-chloro-2-propanone oxime, having a melting point of about 99°–100° C., weighing 157.7 g., from 232.6 g. (purity 86%) (1.01 moles) of 1-bromo-4-(1-propenyl)benzene and 66.5 g. (1.01 moles) of nitrosyl chloride.

| Analyses calculated for $C_9H_9BrClNO$ | | |
|---|---|---|
| | Theoretical | Found |
| C | 41.18 | 41.01 |
| H | 3.46 | 3.43 |
| Br | 30.44 | 30.56 |
| Cl | 13.50 | 13.65 |
| N | 5.34 | 5.20 |

PREPARATION 8

1-(4-Bromophenyl)-1-chloro-2-butanone oxime, weighing 5.27 g., from 12.5 g. (0.059 moles) of 1-bromo-4-(1-butenyl)benzene and 3.88 g. (0.059 moles) of nitrosyl chloride. The analytical sample had a melting point of about 98°–99° C.

| Analyses calculated for $C_{10}H_{11}BrClNO$: | | |
|---|---|---|
| | Theoretical | Found |
| C | 43.43 | 43.63 |
| H | 4.01 | 3.97 |
| Br | 28.89 | 28.77 |
| Cl | 12.82 | 12.76 |
| N | 5.06 | 4.98 |

PREPARATION 9

1-(2,4-Dimethylphenyl)-1-chloro-2-propanone oxime, having a melting point of about 104°–106° C., and weighing 4.79 g., from 6.0 g. (0.04 moles) of 2,4-dimethyl-1-propenylbenzene and 2.96 (0.045 moles) of nitrosyl chloride. Identified by NMR spectrum.

PREPARATION 10

1-Chloro-1-(3-trifluoromethylphenyl)-2-propanone oxime, as a green oil weighing 18.87 g., from 15 g. (0.0806 moles) of 1-trifluoromethyl-3-(1-propenyl)benzene and 9.24 g. (0.14 moles) of nitrosyl chloride. Identified by NMR spectrum.

PREPARATION 11

1-Chloro-1-(4-chlorophenyl)-2-propanone oxime, having a melting point of about 80°–81° C., and weighing 9.09 g., from 15.25 g. (0.10 mole) of 1-chloro-4-(1-propenyl)benzene and 6.88 g. (0.10 mole) of nitrosyl chloride. Identified by IR and NMR spectra.

PREPARATION 12

1-(3,4-Dichlorophenyl)-1-chloro-2-propanone oxime, as an oil, weighing 21.1 g., from 18.7 g. (0.10 mole) of 1,2-dichloro-4-(1-propenyl)benzene and 6.88 g. (0.10 mole) of nitrosyl chloride. The product was identified by its NMR spectrum.

PREPARATION 13

1-(4-Ethylphenyl)-1-chloro-2-propanone oxime, having a melting point of about 39°–49° C., and weighing 21 g., from 22 g. (0.15 moles) of 1-ethyl-4-(1-propenyl)benzene and 9.9 g. (0.15 moles) of nitrosyl chloride. The product was identified by its NMR spectrum.

Utilizing the α-chloro oximes prepared hereinbefore, the novel compounds of this invention were prepared as described in the following operating examples. However, the invention is not to be considered as limited by the examples.

EXAMPLE 1

[[2-(Hydroxyimino)-1-(phenyl)propyl]amino]acetonitrile

The synthesis of this compound is carried out stepwise.

Step A

To a suspension of 11.56 g. (0.125 moles) of aminoacetonitrile hydrochloride in 90 ml. of chloroform, stirred under a nitrogen atmosphere and cooled to about 0° C. in an ice-bath, was added 22.73 g. (0.225 moles) of triethylamine. To the resulting mixture, maintained at a temperature of about 0° C., there was added a solution of 18.35 g. (0.10 mole) of 1-chloro-1-phenyl-2-propanone oxime in 85 ml. of chloroform over a period of about 2 hours. The reaction mixture was then allowed to warm to room temperature over a period of about 1 hour.

Step B

The reaction mixture was washed twice with 100 ml. portions of water, one 100 ml. portion of saturated brine, and dried by filtration through a pad of anhydrous sodium sulfate. The filtrate was reduced to about ½ its volume by concentrating it under reduced pressure, and sufficient hexane was added thereto to restore the original volume. The resulting mixture was allowed to attain about room temperature with stirring, allowing the product to crystallize. After standing in the refrigerator overnight, the mixture was filtered and the crystals remaining on the filter were washed with 75 ml. of cold hexane. In this manner there was obtained 13.22 g. (65% yield) of product identified as [[2-(hydroxyimino)-1-(phenyl)propyl]amino]acetonitrile, having a melting point of about 94.5°–96.5° C. A sample for analysis was recrystallized from ethanol, and had a melting point of about 96°–97.5° C. The product was identified by elemental analyses, NMR and mass spectra.

| Analyses calculated for $C_{11}H_{13}N_3O$: | | |
|---|---|---|
|  | Theoretical | Found |
| C | 65.01 | 65.18 |
| H | 6.45 | 6.55 |
| N | 20.68 | 20.39 |

Following the general procedure of Steps A and B of Example 1, additional hydroxyimino-substituted aminoacetonitriles were prepared. The weights of reactants and products are recorded in the examples which follow.

EXAMPLE 2

[[1-(2-Bromophenyl)-2-(hydroxyimino)propyl]amino]acetonitrile, weighing 1.25 g., from 5.0 g. (0.019 moles) of 1-(2-bromophenyl)-1-chloro-2-propanone oxime, 2.2 g. (0.024 moles) of aminoacetonitrile hydrochloride, and 4.33 g. (0.043 moles) of triethylamine. The analytical sample had a melting point of about 139°–142° C.

| Analyses calculated for $C_{11}H_{12}BrN_3O$: | | |
|---|---|---|
|  | Theoretical | Found |
| C | 46.83 | 46.67 |
| H | 4.29 | 4.14 |
| N | 14.89 | 14.74 |
| Br | 28.32 | 28.56 |

EXAMPLE 3

[[1-(3-Bromophenyl)-2-(hydroxyimino)propyl]amino]acetonitrile, as an oil, which later crystallized, weighing 5.4 g., from 5.0 g. (0.019 moles) of 1-(3-bromophenyl)-1-chloro-2-propanone oxime, 2.2 g. (0.024 moles) of aminoacetonitrile hydrochloride, and 4.33 g. (0.043 moles) of triethylamine. The analytical sample had a melting point of about 96°–98° C.

| Analyses calculated for $C_{11}H_{12}BrN_3O$: | | |
|---|---|---|
|  | Theoretical | Found |
| C | 46.83 | 46.72 |
| H | 4.29 | 4.10 |
| N | 14.89 | 14.67 |

EXAMPLE 4

[[1-(4-Bromophenyl)-2-(hydroxyimino)propyl]amino]acetonitrile, weighing 44.8 g., from 45 g. (0.17 moles) of 1-(4-bromophenyl)-1-chloro-2-propanone oxime, 19.82 g. (0.21 moles) of aminoacetonitrile hydrochloride, and 38.96 g. (0.385 moles) of triethylamine. The analytical sample had a melting point of about 111°–112° C.

| Analyses calculated for $C_{11}H_{12}BrN_3O$: | | |
|---|---|---|
|  | Theoretical | Found |
| C | 46.83 | 46.66 |
| H | 4.29 | 4.10 |
| N | 14.89 | 14.65 |

EXAMPLE 5

[[1-(4-Bromophenyl)-2-(hydroxyimino)butyl]amino]acetonitrile, weighing 3.12 g., from 4.0 g. (0.0145 moles) of 1-(4-bromophenyl)-1-chloro-2-butanone oxime, 1.67 g. (0.018 moles) of aminoacetonitrile hydrochloride, and 3.29 g. (0.033 moles) of triethylamine. The analytical sample had a melting point of about 118.5°–120° C.

| Analyses calculated for $C_{12}H_{14}BrN_3O$: | |
|---|---|
| | Theoretical | Found |
| C | 48.67 | 48.58 |
| H | 4.76 | 4.51 |
| N | 14.19 | 13.93 |
| Br | 26.98 | 27.17 |

EXAMPLE 6

[[1-(2,4-Dimethylphenyl)-2-(hydroxyimino)propyl]amino]acetonitrile, having a melting point of about 133°–134° C., and weighing 2.51 g., from 4.0 g. (0.019 moles) of 1-chloro-1-(2,4-dimethylphenyl)-2-propanone oxime, 2.18 g. (0.024 moles) of aminoacetonitrile hydrochloride, and 4.29 g. (0.043 moles) of triethylamine.

| Analyses calculated for $C_{13}H_{17}N_3O$: | |
|---|---|
| | Theoretical | Found |
| C | 67.51 | 67.58 |
| H | 7.41 | 7.18 |
| N | 18.17 | 18.01 |

EXAMPLE 7

[[2-(Hydroxyimino)-1-[3-trifluoromethyl)phenyl]propyl]amino]acetonitrile, having a melting point of about 101°–103° C., and weighing 1.5 g., from 15 g. (0.059 moles) of 1-chloro-1-(3-trifluoromethylphenyl)-2-propanone oxime, 5.52 g. (0.059 moles) of aminoacetonitrile hydrochloride, and 12.05 g. (0.119 moles) of triethylamine.

| Analyses calculated for $C_{12}H_{12}F_3N_3O$: | |
|---|---|
| | Theoretical | Found |
| C | 53.14 | 53.11 |
| H | 4.46 | 4.37 |
| N | 15.49 | 15.25 |
| F | 21.01 | 21.23 |

EXAMPLE 8

[[1-(4-Chlorophenyl)-2-(hydroxyimino)propyl]amino]acetonitrile, having a melting point of about 119.5°–121° C., and weighing 7.38 g., from 7.5 g. (0.034 moles) of 1-chloro-1-(4-chlorophenyl)-2-propanone oxime, 3.98 g. (0.043 moles) of aminoacetonitrile hydrochloride, and 7.82 g. (0.077 moles) of triethylamine.

| Analyses calculated for $C_{11}H_{12}ClN_3O$: | |
|---|---|
| | Theoretical | Found |
| C | 55.59 | 55.35 |
| H | 5.09 | 5.24 |
| Cl | 14.92 | 14.70 |
| N | 17.68 | 17.69 |

EXAMPLE 9

[[1-(3,4-Dichlorophenyl)-2-(hydroxyimino)propyl]amino]acetonitrile, weighing 1.82 g., from 10 g. of crude 1-chloro-1-(3,4-dichlorophenyl)-2-propanone oxime, 4.58 g. (0.05 moles) of aminoacetonitrile hydrochloride, and 9.0 g. (0.09 moles) of triethylamine. The analytical sample had a melting point of about 106.5°–107.5° C. Identified by IR, NMR and mass spectra. High resolution MS: calculated for $C_{11}H_{11}{}^{35}Cl_2N_3O$: 271.02791; found: 271.02807.

EXAMPLE 10

[1-(4-Ethylphenyl)-2-(hydroxyimino)propylamino]acetonitrile, having a melting point of about 83°–85° C., and weighing 13.6 g., from 21.2 g. (0.10 mole) of 1-chloro-1-(4-ethylphenyl)-2-propanone oxime, 11.6 g. (0.125 moles) of aminoacetonitrile hydrochloride, and 25.2 g. (0.25 moles) of triethylamine. The product was identified by its NMR spectrum.

The following Example illustrates the synthesis of one of the hydroxyimino-substituted aminoacetonitrile starting with a substituted styrene and continuing via the resulting α-chloro oxime without separation and purification of that intermediate α-chloro oxime. The α-chloro oxime was kept in solution and added to a mixture of an aminoacetonitrile (or aminoacetonitrile acid addition salt), an acid uptake agent, and a suitable solvent, all as has been described hereinbefore.

EXAMPLE 11

[1-(4-Bromophenyl)-2-(hydroxyimino)propyl]amino]acetonitrile

A solution of 27.7 kg. of 1-bromo-4-(1-propenyl)benzene (purity, 90%) in 110 l. methylene chloride was cooled to about 0° C. and saturated with hydrogen chloride. Nitrosyl chloride (8.74 kg.) was bubbled into the mixture at such a rate that the temperature was maintained below 10° C. Addition of hydrogen chloride was continued concurrently with the nitrosyl chloride addition at such a rate that saturation of the mixture with hydrogen chloride was maintained. When addition of nitrosyl chloride was complete the mixture was stirred for an additional 15 minutes under hydrogen chloride saturation, then purged with nitrogen to remove excess nitrosyl chloride and hydrogen chloride. The mixture was washed with three 60 l. portions of water and the layers separated. The methylene chloride layer, containing the α-chloro oxime product, was dropped slowly into a second reaction vessel containing a mixture of 11.6 kg. of aminoacetonitrile hydrochloride, 25.2 kg. of triethylamine, and 120 l. of methylene chloride cooled to about 10° C., so that the reaction temperature was maintained below 20° C. The mixture was allowed to warm to about 25° C. over about 2 hours, then washed with three 60 l. portions of water. The methylene chloride layer was carefully concentrated under vacuum to a volume of about 100 l. The temperature of the solution was adjusted to about 40° C. and 100 l. of hexane, warmed to a temperature of about 40° C., was added with stirring. The product crystallized as the mixture was slowly cooled and stirred at room temperature overnight. The mixture was cooled briefly to about 0°–5° C., then filtered, and the crystals washed with hexane. There was thus obtained 18.7 kg. of [[1-(4-bromophenyl)-2-(hydroxyimino)propyl]amino]acetonitrile, having a m.p. of about 108°–110° C. The yield was calculated to be about 52.5% of theory based on the weight of 1-bromo-4-(1-propenyl)benzene used. The purity of the product was estimated to be about 98% by a gas chromatographic method.

The above examples illustrate the preparation of the novel hydroxyimino-substituted aminoacetonitriles, which are valuable intermediates in the synthesis of substituted 2-aminopyrazines used in the preparation of benzoylpyrazinylureas, insecticides.

I claim:
1. A compound of the formula

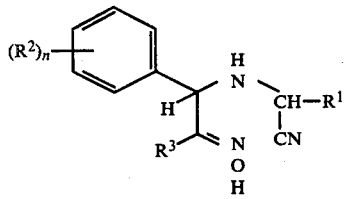
(I)

wherein
R¹ is hydrogen or $C_1$–$C_4$ alkyl;
R² is hydrogen, halo, $C_1$–$C_3$ alkyl, or trifluoromethyl;
n is 0, 1 or 2, with the proviso that when n=2, only one ortho position may be substituted; and
R³ is $C_1$–$C_4$ alkyl.

2. A compound as in claim 1, said compound being [[2-(hydroxyimino)-1-(phenyl)propyl]amino]acetonitrile.

3. A compound as in claim 1, said compound being [[1-(4-bromophenyl)-2-(hydroxyimino)propyl]amino]acetonitrile.

4. A compound as in claim 1, said compound being [[1-(2-bromophenyl)-2-(hydroxyimino)propyl]amino]acetonitrile.

5. A compound as in claim 1, said compound being [[1-(3-bromophenyl)-2-(hydroxyimino)propyl]amino]acetonitrile.

6. A compound as in claim 1, said compound being [[1-(4-bromophenyl)-2-(hydroxyimino)butyl]amino]acetonitrile.

7. A compound as in claim 1, said compound being [[1-(2,4-dimethylphenyl)-2-(hydroxyimino)propyl]amino]acetonitrile.

8. A compound as in claim 1, said compound being [[2-(hydroxyimino)-1-(3-trifluoromethylphenyl)propyl]amino]acetonitrile.

9. A compound as in claim 1, said compound being [[1-(4-chlorophenyl)-2-(hydroxyimino)propyl]amino]acetonitrile.

10. A compound as in claim 1, said compound being [[1-(3,4-dichlorophenyl)-2-(hydroxyimino)propyl]amino]acetonitrile.

11. A compound as in claim 1, said compound being [[1-(4-ethylphenyl)-2-(hydroxyimino)propyl]amino]acetonitrile.

* * * * *

UNITED STATES PATENT AND TRADEMARK OFFICE
CERTIFICATE OF CORRECTION

PATENT NO. : 4,199,525
DATED : April 22, 1980
INVENTOR(S) : Charles J. Barnett

It is certified that error appears in the above-identified patent and that said Letters Patent are hereby corrected as shown below:

Column 6, line 28, "ophenone in 30 ml." should read --ophenone [prepared by the procedure of Kindler and Li, Ber. 74, 321 (1941)] in 30 ml.--

Column 7, line 20,, "-3+ C.," should read ---3° C.,--.

Column 7, line 47, "90-92 C.," should read --90-92° C.,--.

Signed and Sealed this

Twenty-second Day of July 1980

[SEAL]

Attest:

SIDNEY A. DIAMOND

Attesting Officer

Commissioner of Patents and Trademarks